US011457522B2

(12) United States Patent
Kim (10) Patent No.: US 11,457,522 B2
(45) Date of Patent: Sep. 27, 2022

(54) SKIN TREATMENT APPARATUS USING FRACTIONAL PLASMA

(71) Applicant: SEOULIN MEDICARE CO., LTD., Hwaseong-si (KR)

(72) Inventor: Byoung Choul Kim, Seongnam-si (KR)

(73) Assignee: SEOULIN MEDICARE CO., LTD., Hwaseong-si (KR)

( * ) Notice: Subject to any disclaimer, the term of this patent is extended or adjusted under 35 U.S.C. 154(b) by 784 days.

(21) Appl. No.: 16/347,020

(22) PCT Filed: Sep. 10, 2018

(86) PCT No.: PCT/KR2018/010535
§ 371 (c)(1),
(2) Date: May 2, 2019

(87) PCT Pub. No.: WO2019/107714
PCT Pub. Date: Jun. 6, 2019

(65) Prior Publication Data
US 2020/0084871 A1 Mar. 12, 2020

(30) Foreign Application Priority Data
Nov. 29, 2017 (KR) .......................... 10-2017-0161579

(51) Int. Cl.
*H05H 1/24* (2006.01)
*A61N 1/44* (2006.01)
*H05H 1/46* (2006.01)

(52) U.S. Cl.
CPC ............. *H05H 1/2406* (2013.01); *A61N 1/44* (2013.01); *H05H 1/46* (2013.01); *H05H 1/2425* (2021.05)

(58) Field of Classification Search
USPC .................................................... 315/111.21
See application file for complete search history.

(56) References Cited

U.S. PATENT DOCUMENTS

| 5,935,460 A * | 8/1999 | Mori ......................... H05H 1/46 83/16 |
| 7,255,062 B1 * | 8/2007 | Higman ................... H05H 1/46 118/723 AN |

(Continued)

FOREIGN PATENT DOCUMENTS

| DE | 102007030915 A1 * | 1/2009 | ............... A61N 1/40 |
| KR | 10-2012-0136524 A | 12/2012 | |

(Continued)

*Primary Examiner* — Srinivas Sathiraju
(74) *Attorney, Agent, or Firm* — Rabin & Berdo, P.C.

(57) ABSTRACT

The present invention relates to a skin treatment apparatus using plasma. A plasma generator (400) comprises an electrode plate (420), an upper dielectric body (430), independent electrode portions (440) and a lower dielectric body (450). The independent electrode portion is an FPCB or a silver paste positioned a fixed distance away. According to the present invention, the electrode portions each independently work and thus prevent unevenness of plasma and enable the plasma to be generated evenly. According to the present invention, the plasma generator having such configuration is easily formed into a convex shape, and a convex plasma generator is suitable for a curved skin object such as the palm. The convex plasma generator can generate more even plasma and is particularly more effective for a long cylindrical object to be treated, such as the woman's vagina.

4 Claims, 7 Drawing Sheets

(56) References Cited

U.S. PATENT DOCUMENTS

| | | | | |
|---|---|---|---|---|
| 8,267,884 B1* | 9/2012 | Hicks | A61B 18/042 | 604/23 |
| 9,131,597 B2* | 9/2015 | Taft | H05H 1/46 | |
| 9,498,637 B2* | 11/2016 | Sanders | A61B 18/042 | |
| 10,039,927 B2* | 8/2018 | Watson | H05H 1/2406 | |
| 10,262,836 B2* | 4/2019 | Chang | C01B 13/11 | |
| 10,300,159 B2* | 5/2019 | Morfill | F24C 15/20 | |
| 10,391,327 B2* | 8/2019 | Skiera | A61N 1/44 | |
| 10,830,254 B2* | 11/2020 | Goto | F04D 29/526 | |
| 11,089,668 B2* | 8/2021 | Trutwig | A61L 2/0011 | |
| 2008/0302761 A1* | 12/2008 | Hirayama | H05H 1/46 | 134/1.1 |
| 2009/0121638 A1* | 5/2009 | Price | H05H 1/46 | 315/111.21 |
| 2011/0022043 A1* | 1/2011 | Wandke | H05H 1/2406 | 606/41 |
| 2011/0045205 A1* | 2/2011 | Rostaing | H05H 1/46 | 118/723 AN |
| 2012/0018410 A1* | 1/2012 | Zakrzewski | H05H 1/46 | 219/121.48 |
| 2012/0259270 A1* | 10/2012 | Wandke | H05H 1/24 | 604/23 |
| 2013/0064726 A1* | 3/2013 | Morfill | A61L 2/14 | 422/186.21 |
| 2013/0072858 A1* | 3/2013 | Watson | H01J 37/3244 | 604/23 |
| 2014/0147333 A1* | 5/2014 | Morfill | A61L 2/14 | 422/186 |
| 2014/0188037 A1* | 7/2014 | Jacofsky | H05H 1/2406 | 604/23 |
| 2014/0207053 A1* | 7/2014 | Morfill | A61L 2/0011 | 604/23 |
| 2015/0343231 A1* | 12/2015 | Sanders | A61L 2/0011 | 607/2 |
| 2015/0373824 A1* | 12/2015 | Nettesheim | H01L 41/107 | 315/111.21 |
| 2016/0271419 A1* | 9/2016 | Varghese | A61N 1/44 | |
| 2016/0331989 A1* | 11/2016 | Cho | A61N 1/326 | |
| 2017/0043150 A1* | 2/2017 | Kim | A61H 23/0218 | |
| 2017/0326347 A1* | 11/2017 | Kalghatgi | A61B 18/042 | |
| 2018/0099149 A1* | 4/2018 | Pai | A61L 2/14 | |
| 2018/0140824 A1* | 5/2018 | Pemen | A61N 1/0468 | |
| 2018/0335055 A1* | 11/2018 | Goto | F04D 29/687 | |
| 2020/0038673 A1* | 2/2020 | Yildirim | A61L 2/14 | |
| 2020/0069956 A1* | 3/2020 | de Penning | A61B 18/042 | |
| 2020/0069957 A1* | 3/2020 | Kim | A61N 1/44 | |
| 2020/0084871 A1* | 3/2020 | Kim | H05H 1/2406 | |
| 2020/0108262 A1* | 4/2020 | Kim | A61N 1/44 | |

FOREIGN PATENT DOCUMENTS

| | | |
|---|---|---|
| KR | 10-1407672 B1 | 6/2014 |
| KR | 10-1568380 B1 | 11/2015 |
| KR | 10-2016-0134593 A | 11/2016 |
| KR | 10-2017-0054716 A | 5/2017 |

* cited by examiner

SKIN TREATMENT APPARATUS USING FRACTIONAL PLASMA

TECHNICAL FIELD

The present invention relates to a skin treatment apparatus using plasma, and more particularly, to a skin treatment apparatus using fractional plasma, which includes a dielectric, induces dielectric barrier discharge between skin and a plasma generator to generate soft plasma, and includes an independent electrode using a plurality of pieces of silver paste so as to prevent a phenomenon of uneven plasma.

BACKGROUND ART

States of matter may be classified into solid, liquid, and gas. When energy is applied to a gaseous-state material, an electron is separated from an atom or molecule such that the gaseous state becomes a plasma state in which electrons, ions, and neutral particles (molecules and atoms) are mixed.

In such a plasma state, electrons may be easily accelerated by a variety of methods, neutral particles collide with molecules of a treated material to generate chemically active species, and ions create conditions, in which a chemical reaction may occur, on a surface of the treated material such that the active species cause an active chemical reaction on the surface.

That is, in this plasma, for example, oxy-, hydroxyl-, and N-radical, electronically excited atoms or molecules, and chemically active species such as ultraviolet (UV) photons, ions, radicals, and the like are included, which move along an electric field and excite and sterilize an inside and outside of an affected part while lightly and softly tapping on the affected part.

Although it is easier to generate plasma in a vacuum state at a low pressure of 1 mTorr to 100 Torr than at atmospheric pressure, when to generate plasma at such a low pressure, a variety of constraints such as manufacturing a vacuum container and mounting a vacuum pump to maintain a vacuum, and the like are necessary. Due to these reasons, a lot of studies on a method of generating plasma at atmospheric pressure which is not vacuum have been performed such that it is possible to generate plasma at or above atmospheric pressure.

Due to the properties of plasma and development of a method of generating plasma, plasma has been used in a variety of industrial fields. Practical attempts using the technique have significantly increased in a medical field such as sterilization of microbes, hemostasis of a wound, dental bleaching, apoptosis inducement of cancer cells, and the like. Particularly, a possibility of a technique of using plasma for skin treatment has been verified earlier than other fields and an in-depth study thereon has been performed.

Meanwhile, plasma may be classified into thermal plasma discharge and nonthermal plasma discharge according to a method of generating plasma. The thermal plasma discharge is a method of ionizing a gas using heat, and the nonthermal plasma method is a method of ionizing a gas by heating electrons mainly while minimizing heating of the gas. The nonthermal plasma method is also called non-equilibrium plasma because only electrons are at a high temperature and other ions and neutral particles remain at a low temperature, which is not thermally equilibrated.

Nonthermal plasma production is generated in a following process. When two flat conductors are spaced at a certain distance d apart and a voltage V is applied to the conductors, an electric field E is generated in a condition of $E=V/d$. Here, when a level of voltage becomes a certain degree or higher, charged particles (electrons) are accelerated by the electric field E such that charged particles (electrons) receive energy and then collide with neutral gas atoms or molecules. Accordingly, atoms and molecules are ionized such that there is formed a plasma state in which electrons, ions, and neutral particles (molecules and atoms) are mixed.

Figure 1:
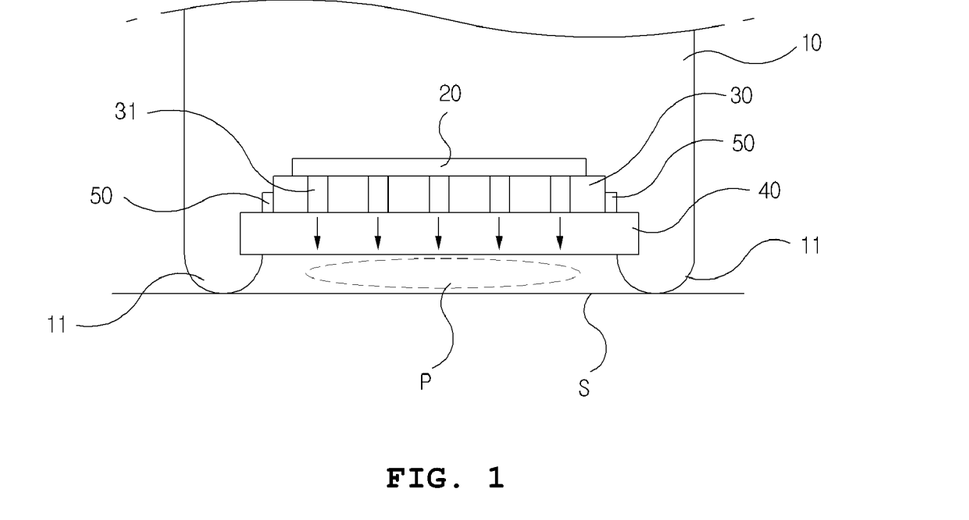
FIG. 1 is a conventional skin treatment apparatus using plasma.

A plasma generator of a related art (KR10-1568380 B1), as shown in FIG. 1, is provided as a tip at a front end of a handpiece type cylindrical housing 10 and includes an electrode 20 receiving a frequency from a transformer, a disc-shaped substrate 30 which is located on a lower surface of the electrode 20 and includes a plurality of through holes 31 formed at a part in contact with the electrode 20 at vertically equal intervals, and a dielectric 40 in contact with a lower surface of the substrate 30.

The through holes 31 are formed at the substrate 30 to be similar to holes of a shower head, and insides of the through holes 31 may be coated or plated with a conducting material. The dielectric 40 may include a material such as quartz, sapphire, glass, ceramic, a polymer film, and the like and may have a thickness of 0.1 mm to 3 mm and relative permittivity of 4 to 18.

Accordingly, power transferred from the electrode 20 is transferred to the dielectric 40 through the through holes 31 of the substrate 30 like a shower such that an R-L-C series circuit is formed between the dielectric 40 and skin S. Accordingly, the skin S becomes a circuit having low impedance such that a weak current, which does not harm a human body, flows therein. Here, between the skin S and the dielectric 40, which come into contact with each other, plasma P is generated by a soft dielectric barrier discharge of a plasma shower method.

However, in the related art, a high frequency and a high voltage are applied to the electrode 20 and power transferred from the electrode 20 is transferred to the dielectric 40 through the through holes 31 of the substrate 30 like a shower such that plasma is generated between the dielectric 40 and the skin S. Here, since all the plurality of through holes 31 are connected to one electrode 20, the plurality of through holes 13 do not operate as independent electrodes such that a phenomenon in which plasma is not evenly generated in the plurality of through holes 13, that is, an unevenness phenomenon may occur.

Also, the conventional plasma generator has a structure which is adequate for a flat part overall such as a face and the back of a hand but is inadequate for a curved object to be treated such as a palm, and particularly, is not applicable to a long cylindrical object to be treated such as a woman's vagina.

DISCLOSURE

Technical Problem

The present invention is directed to providing a skin treatment apparatus which includes independent electrode portions which are formed of silver paste or flexible printed circuit boards (FPCBs) between an upper dielectric and a lower dielectric while being spaced at certain distances apart.

The present invention is also directed to providing a skin treatment apparatus including a plasma generator having a convex shape, which is any one of a cylindrical shape, a cylindrical fragment, a spherical shape, and a shape of a part of sphere, to treat skin.

Technical Solution

One aspect of the present invention provides a skin treatment apparatus, which treats skin using plasma generated by a plasma generator. The apparatus includes a high voltage module and the plasma generator to generate plasma and treats skin using plasma generated by the plasma generator. Here, the plasma generator includes a power connector connected to the high voltage module, an electrode plate having one concave surface connected to the power connector and another convex surface facing the skin, an upper dielectric which has a semicylindrical shape having an open top and accommodates the electrode plate, a plurality of independent electrode portions which surround a convex part of the upper dielectric and have one concave surface facing the upper dielectric and another convex surface facing the skin while electrodes are spaced at certain distances apart, and a lower dielectric which has a semicylindrical shape having an open top and accommodates the independent electrode portions, wherein power is applied to the electrode plate through the power connector and power from the electrode plate is supplied to the upper dielectric, the independent electrode portions, and the lower dielectric such that plasma is generated in a space between the lower dielectric and the skin.

An upper circumferential part of the lower dielectric may protrude outward by a certain length.

The independent electrode portions may be silver paste or flexible printed circuit boards (FPCBs).

Advantageous Effects

According to the present invention, a phenomenon of uneven plasma may be prevented by including independent electrode portions between an upper dielectric and a lower dielectric, which are formed of silver paste or flexible printed circuit boards (FPCBs) spaced at certain intervals apart.

According to the present invention, a curved object to be treated such as a palm may be treated effectively by including a convex plasma generator. Particularly, when the generator includes a cylindrical body and an end of a cylindrical body, a long cylindrical object to be treated such as a woman's vagina may be treated effectively.

MODES OF THE INVENTION

Hereinafter, exemplary embodiments of the present invention will be described in detail with reference to the attached drawings.

Figure 2:
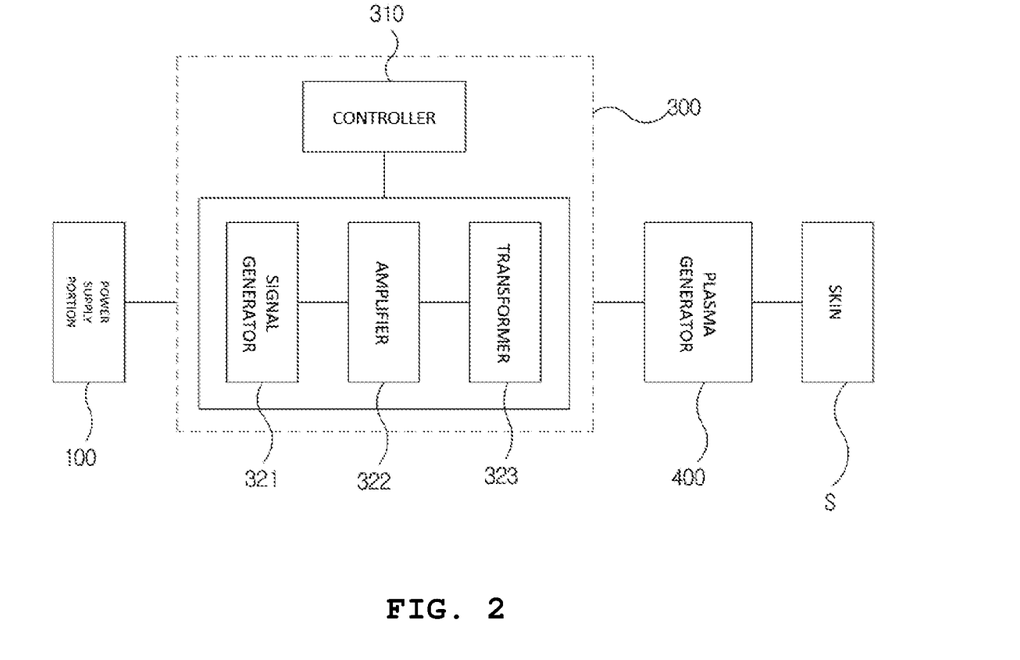
FIG. 2 is a block diagram illustrating an entire structure of the present invention.

A skin treatment apparatus using plasma according to the present invention includes, as shown in FIG. 2, a power supply portion 100, a high voltage module 300, and a plasma generator 400. The high voltage module 300 includes a controller 310, a signal generator 321, an amplifier 322, and a transformer 323.

The power supply portion 100 may be an external power source or may be a miniaturized battery for being portable.

The controller 310 of the high voltage module 300 controls direct current (DC) power output from the power supply portion 100 to be converted into high-frequency and high-voltage alternating current (AC) power. The signal generator 321 of the high voltage module 300 generates a frequency equal to or higher than 20 kHz, and the amplifier 322 of the high voltage module 300 is matched at an impedance of 5 to 50 W.

The transformer 323 of the high voltage module 300 supplies a frequency output from the amplifier 322 of the high voltage module 300 to the plasma generator 400 to cause generation of plasma.

Figure 3:
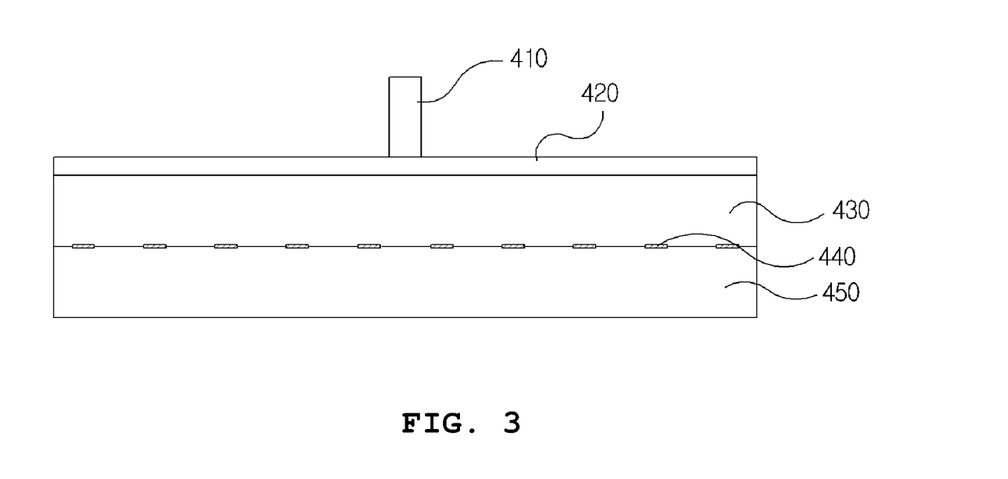
FIG. 3 is a view illustrating main parts of a plasma generator according to the present invention.

FIG. 3 illustrates main parts of the plasma generator 400 which generates plasma using the high-voltage and high-frequency power output from the high voltage module 300.

The plasma generator 400 includes a power connector 410, which transfers power from the transformer 323 of the high voltage module 300, an electrode plate 420, which receives high voltage and high frequency through the power connector 410, and an upper dielectric 430 and a lower dielectric 450 below the electrode plate 420. A plurality of independent electrode portions 440 are printed between the upper dielectric 430 and the lower dielectric 450 while being spaced at certain distances apart.

The skin treatment apparatus using plasma, which includes the above components, according to the present invention operates as follows.

First, when the skin treatment apparatus according to the present invention is located on a part to be treated and an operation-start button is pushed, the power supply portion 100 supplies DC power to the high voltage module 300 and the high voltage module 300 converts the DC power into high-voltage and high-frequency AC power using the controller 310, the signal generator 321, the amplifier 322, and the transformer 323 and supplies the AC power to the electrode plate 420 through the power connector 410 of the plasma generator 400.

The power supplied to the electrode plate 420 passes through the upper dielectric 430 and passes through the independent electrode portions 440 printed between the upper dielectric and the lower dielectric.

Figure 4:
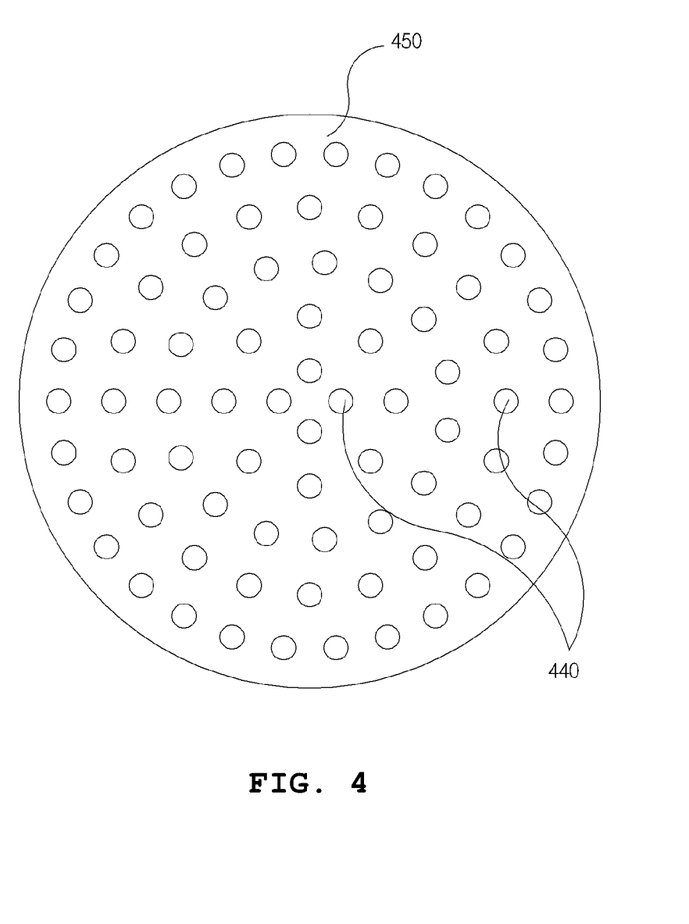
FIG. 4 is a view illustrating independent electrode portions of the plasma generator according to the present invention.

A shape of the independent electrode portions 440 may be a plurality of pieces of silver paste or flexible printed circuit boards (FPCBs) spaced at certain distances apart as shown in FIG. 4.

Figure 5:
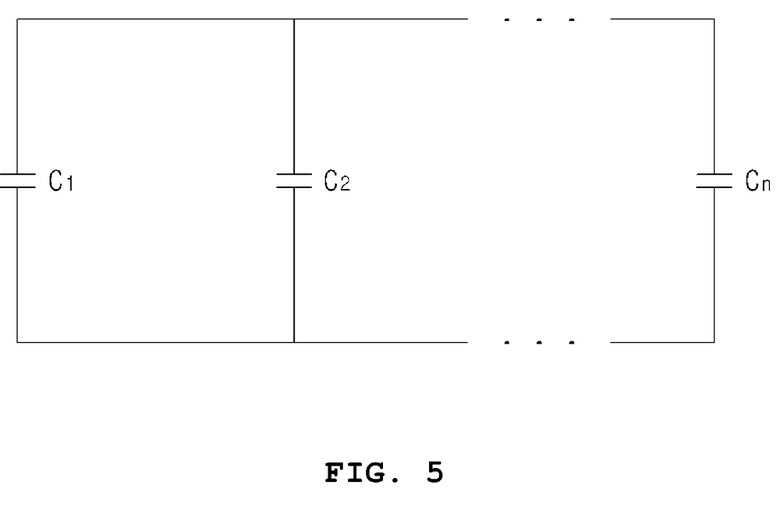
FIG. 5 is an equivalent circuit of the independent electrode portions of FIG. 4.

The independent electrode portion 440 is shown as an equivalent circuit as shown in FIG. 5. That is, each of the independent electrode portions 440 functions as a cell capacitor and may be understood as C1, C2, . . . , and Cn.

Also, values of C1, C2, . . . , and Cn may be adjusted by adjusting cross-sectional areas of the independent electrode portions. That is, since capacitance is proportional to a cross-sectional area, capacitance of the cell capacitor may be increased by increasing the cross-sectional area of the independent electrode portion or may be decreased by decreasing the cross-sectional area of the independent electrode portion. Also, each of the cell capacitors may have the same capacitance.

As described above, according to the present invention, since the electrode portions including the plurality of pieces of silver paste or FPCBs are not connected directly to the electrode plate 420 and operate independently, a phenomenon of existing inventions, in which plasma is collected on one side, may be prevented such that plasma may be generated evenly in each of the independent electrode portions.

Also, according to the present invention, a convex shape, which will be described below, may be easily formed by including thin independent electrode portions like silver paste or FPCBs. Among objects to be treated, an object having a curved shape such as a palm is present and it is difficult to treat the object using a flat plasma generator. In this case, when the plasma generator 400 according to the present invention has a convex shape, the object to be treated which has a curved shape like a palm may be treated effectively.

Also, the convex-shaped plasma generator may generate a more even amount of plasma and will be described with reference to FIG. 6.

Figure 6:
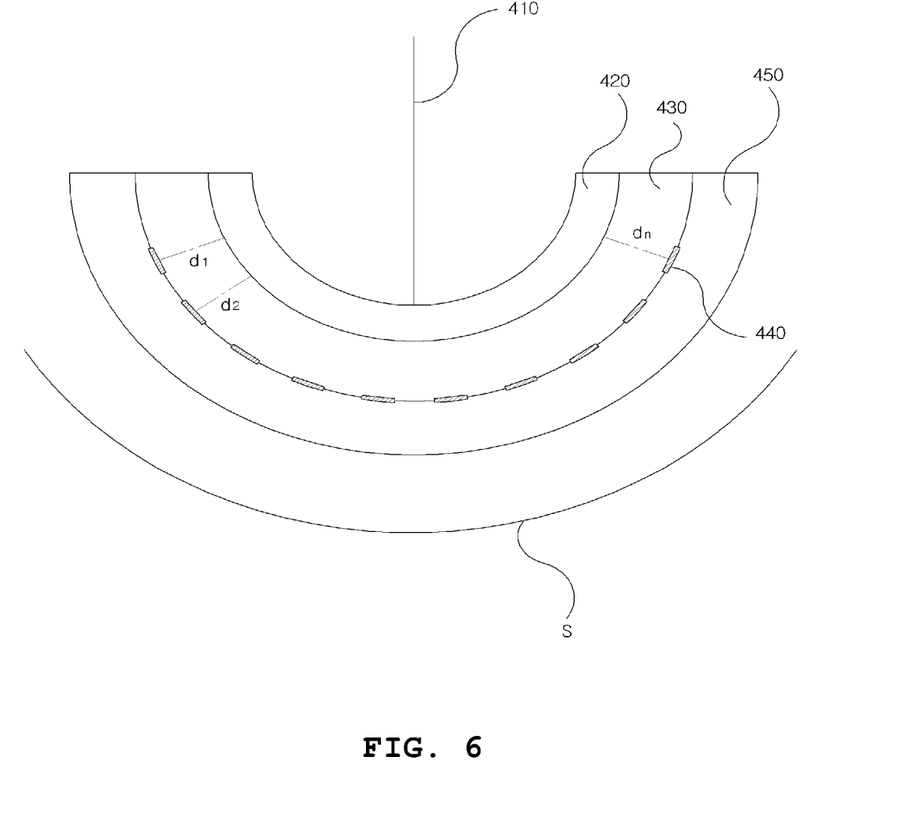
FIG. 6 is a view illustrating the plasma generator, which is convex, according to the present invention.

Since components of the plasma generator of FIG. 6, that is, all of an electrode plate, an upper dielectric, and a lower dielectric have convex shapes, all distances d1, d2, . . . , and do from the electrode plate 420 to the independent electrode portions 440 are equal. Since capacitance is influenced by a distance between two electrodes and such distances are equal, capacitances between the electrode plate 420 and the independent electrode portions are uniform such that even plasma may be emitted toward the skin.

When the plasma generator configured as described has a convex shape, for example, in case of a cylindrical fragment or a cylindrical shape, particularly, there is present an effect of treating a long cylindrical skin like a woman's vagina.

Figure 7:
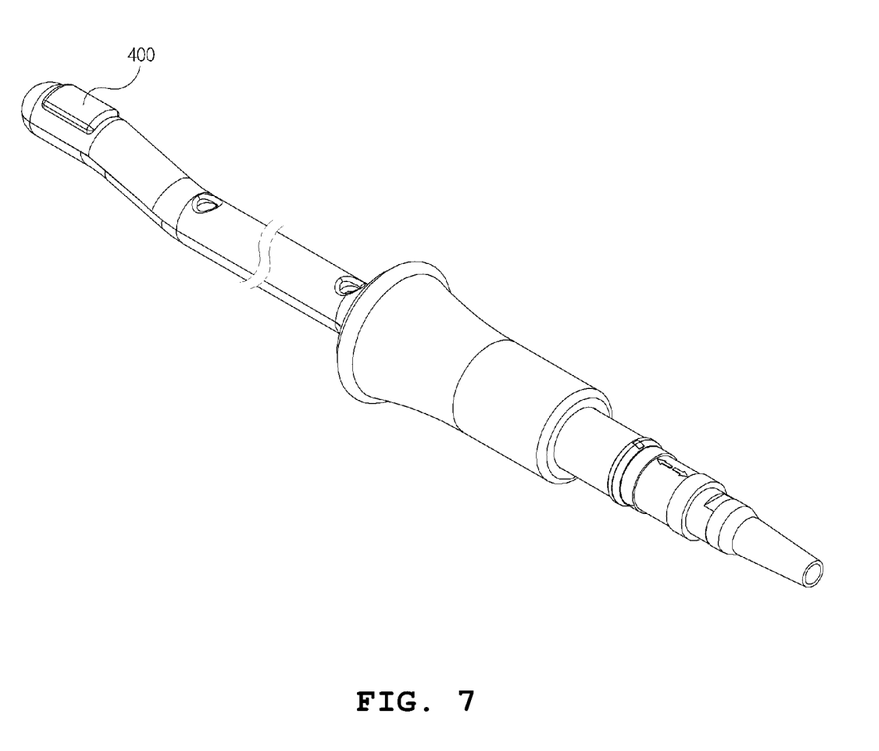
FIG. 7 is a view illustrating the plasma generator according to the present invention, which has a convex cylindrical fragment attached along an outer circumferential surface of a skin treatment apparatus.

As shown in FIG. 7, the plasma generator 400 may have a convex shape (cylindrical fragment) such that the plasma generator 400 may be attached along an outer circumferential surface of an end of the skin treatment apparatus in an arch shape within a range of 30° to 180°. Preferably, the arch shape is formed to be 90°.

Here, the plasma generator may have a size including a width of 8 mm and a length of 20 mm.

Figure 8:
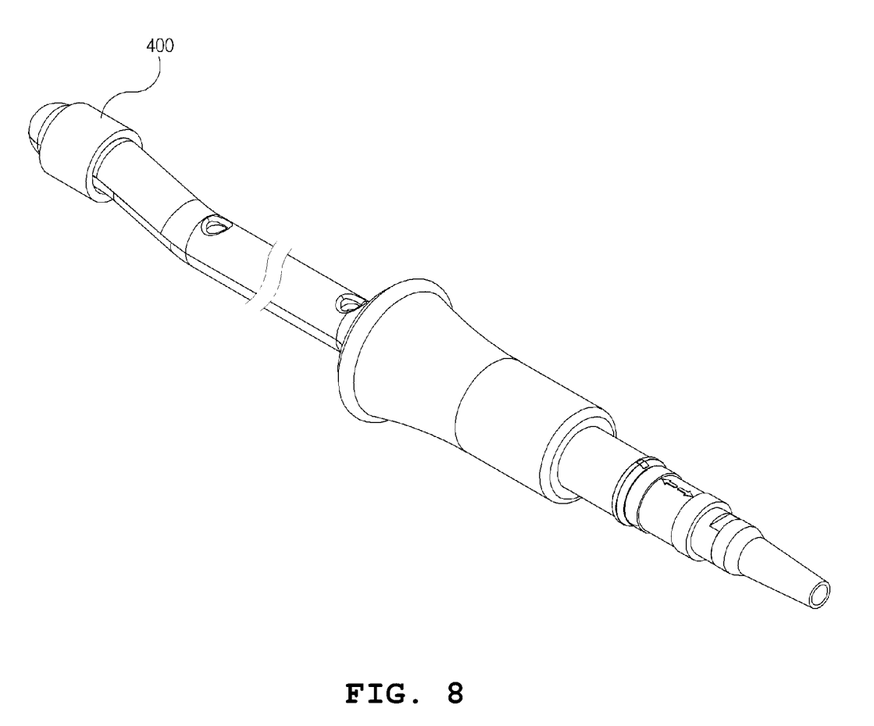
FIG. 8 is a view illustrating the plasma generator according to the present invention, which has a convex cylindrical shape and is attached to an entirety of the outer circumferential surface of the skin treatment apparatus.

Also, as shown in FIG. 8, the plasma generator 400 may have a convex shape (cylindrical shape) so as to be attached to an entirety of the outer circumferential surface of the end of the skin treatment apparatus. Here, also, the plasma generator may have a size including a length of 20 mm.

Figure 9:
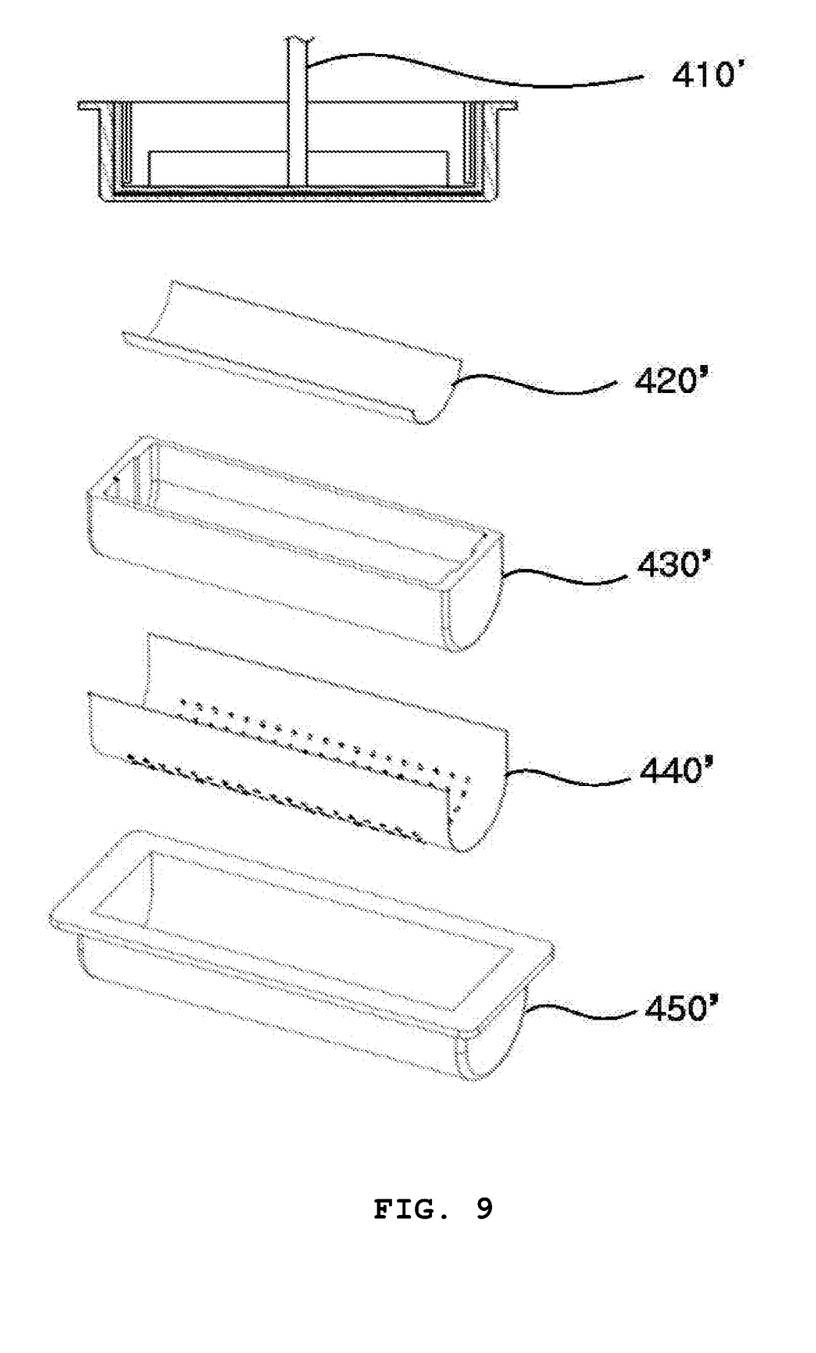
FIG. 9 is a view illustrating another embodiment of the plasma generator according to the present invention.

FIG. 9 illustrates another embodiment of the plasma generator.

An electrode plate 420', which receives a high voltage and a high frequency through a power connector 410', has concave one surface connected to the power connector 410' and another convex surface which faces skin.

Also, an upper dielectric 430', which accommodates the electrode plate 420', has a semicylindrical shape having an open top.

Also, a plurality of independent electrode portions 440' surround a convex part of the upper dielectric 430', and have one concave surface facing the upper dielectric 430' and another convex surface facing the skin S, while electrodes are spaced at certain distances apart.

Also, a lower dielectric 450' has a semicylindrical shape having an open top and includes an upper circumferential part which protrudes outward by a certain length to accommodate the independent electrode portion 440'.

A case, in which silver paste is printed between two dielectrics while being spaced at certain distances apart and the dielectrics have convex shapes as described above, is more effective to an object to be treated which has a long cylindrical shape.

The above-described skin treatment apparatus using plasma according to the present invention is not limited to the embodiments and may have a range of technical mind of being modified and executed by one of ordinary skill in the art without departing from the technical concept of the following claims.

What is claimed is:

1. A skin treatment apparatus using fractional plasma comprising:
   a high voltage module and
   a plasma generator to generate plasma and treats a treatment surface on a skin using plasma generated by the plasma generator, wherein the plasma generator comprises:
      a power connector connected to the high voltage module;
      an electrode plate having a concave surface connected to the power connector and a convex surface facing the treatment surface on a skin;
      an upper dielectric having a semicylindrical shape with an open top and configured to accommodate the electrode plate;
      a plurality of independent electrode portions configured to surround a convex part of the upper dielectric and having a concave surface facing the upper dielectric and a convex surface facing the treatment surface on a skin, the electrode portions being mechanically and electrically spaced apart by certain distances and not directly connected to any external power source; and
      a lower dielectric having a semicylindrical shape with an open top and configured to accommodate the independent electrode portions,
   wherein power is applied to the electrode plate through the power connector and power from the electrode plate is supplied to the upper dielectric, the independent electrode portions, and the lower dielectric such that plasma is generated in a space between the lower dielectric and the treatment surface on a skin, and
   wherein the treatment surface on a skin acts as a grounded electrode.

2. The skin treatment apparatus of claim 1, wherein an upper peripheral part of the lower dielectric protrudes outward by a certain length.

3. The skin treatment apparatus of claim 1, wherein the independent electrode portions are silver paste or flexible printed circuit boards (FPCBs).

4. The skin treatment apparatus of claim 1, wherein the independent electrode portions act as capacitors.

* * * * *